(12) United States Patent
Chow et al.

(10) Patent No.: US 7,754,768 B2
(45) Date of Patent: *Jul. 13, 2010

(54) METHODS AND COMPOSITIONS FOR MODULATING ALPHA ADRENERGIC RECEPTOR ACTIVITY

(75) Inventors: Ken Chow, Newport Coast, CA (US); Daniel W. Gil, Corona Del Mar, CA (US); Wenkui Ken Fang, Irvine, CA (US); Michael E. Garst, Newport Beach, CA (US); Larry A. Wheeler, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/024,609

(22) Filed: Feb. 1, 2008

(65) Prior Publication Data

US 2008/0132576 A1    Jun. 5, 2008

Related U.S. Application Data

(60) Division of application No. 10/039,827, filed on Oct. 19, 2001, now Pat. No. 7,335,803, which is a continuation-in-part of application No. 09/548,410, filed on Apr. 13, 2000, now Pat. No. 6,313,172.

(51) Int. Cl.
*A61K 31/17* (2006.01)
(52) U.S. Cl. .................. 514/587; 514/913
(58) Field of Classification Search ........... 514/587, 514/913
See application file for complete search history.

(56) References Cited

FOREIGN PATENT DOCUMENTS

| IO | 1 499 485 | 2/1978 |
|---|---|---|
| WO | WO 92/0073 | 1/1992 |
| WO | WO 01/78702 | 10/2001 |
| WO | WO 01/78703 | 10/2001 |

OTHER PUBLICATIONS

Dirig et al, "Characterization of variables defining hindpaw withdrawal latency evoked by radiant thermal stimuli", J. Neurosci. Methods 76: 183-191 (1997).
Kim et al, "An experimental model for peripheral neuropathy produced by segmental spinal nerve ligation in the rat", Pain 50, 355-363 (1992).
Hargreaves et al, "A new and sensitive method for measuring thermal nociception in cutaneous hyperalgesia", Pain 32, 77-88 (1988).
Dixon, "Efficient Analysis of Experimental Observations", Ann. Rev. Pharmacol. Toxicol. 20: 441-462 (1980).
CA: 93: 142669 abs of Rozvoj Farm. Ramci Ved.-Tech. Revoluce, Sb. Prednasek Sjezdu Cesk. Farm. Spol., 7th Meeting date 1977 by Reiter et al pp. 121-130.
CA:93:132428 abs of Eur. j. Med. Chem.-Chim. Ther. 15(1) by Reiter et al pp. 41-53.
MEDLINE: 95239789 abs of Journal of neurotrauma by Staub 11(6) pp. 679-690.
CA: 111:105918 abs of W09404531 by Warshawsky et al.

*Primary Examiner*—Zohreh A Fay
(74) *Attorney, Agent, or Firm*—John E. Wurst; Allergan, Inc.

(57) ABSTRACT

Methods and compositions for the treatment of pain and intraocular pressure. Particularly disclosed are new compositions for the treatment of chronic pain, glaucoma and methods for their use.

3 Claims, No Drawings

METHODS AND COMPOSITIONS FOR MODULATING ALPHA ADRENERGIC RECEPTOR ACTIVITY

CROSS REFERENCE TO RELATED APPLICATIONS

This application is a divisional of U.S. patent application Ser. No. 10/039,827 filed Oct. 19, 2001, now U.S. Pat. No. 7,335,803 which is a continuation in part of U.S. patent application Ser. No. 09/548,410 filed Apr. 13, 2000, now U.S. Pat. No. 7,335,803, which is hereby incorporated by reference herein.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes.

Functional differences between $\alpha_1$ and $\alpha_2$ receptors have been recognized, and compounds which exhibit selective binding between these two subtypes have been developed. Thus, in WO 92/0073, the selective ability of the R(+) enantiomer of terazosin to selectively bind to adrenergic receptors of the $\alpha_1$ subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, was said to be limited by their $\alpha_2$ adrenergic receptor mediated induction of increased plasma catecholamine concentration and the attendant physiological sequelae (increased heart rate and smooth muscle contraction).

For a general background on the α-adrenergic receptors, the reader's attention is directed to Robert R. Ruffolo, Jr., α-Adrenoreceptors: Molecular Biology, Biochemistry and Pharmacology, (Progress in Basic and Clinical Pharmacology series, Karger, 1991), wherein the basis of $\alpha_1/\alpha_2$ subclassification, the molecular biology, signal transduction, agonist structure-activity relationships, receptor functions, and therapeutic applications for compounds exhibiting α-adrenergic receptor affinity was explored.

The cloning, sequencing and expression of alpha receptor subtypes from animal tissues has led to the subclassification of the $\alpha_1$ adrenoreceptors into $\alpha_{1A}$, $\alpha_{1B}$, and $\alpha_{1D}$. Similarly, the $\alpha_2$ adrenoreceptors have also been classified $\alpha_{2A}$, $\alpha_{2B}$, and $\alpha_{2C}$ receptors. Each $\alpha_2$ receptor subtype appears to exhibit its own pharmacological and tissue specificities. Compounds having a degree of specificity for one or more of these subtypes may be more specific therapeutic agents for a given indication than an $\alpha_2$ receptor pan-agonist (such as the drug clonidine) or a pan-antagonist.

Among other indications, such as the treatment of glaucoma, hypertension, sexual dysfunction, and depression, certain compounds having alpha 2 adrenergic receptor agonist activity are known analgesics. However, many compounds having such activity do not provide the activity and specificity desirable when treating disorders modulated by alpha-2 adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

British Patent 1 499 485, published Feb. 1, 1978 describes certain thiocarbamide derivatives; some of these are said to be useful in the treatment of conditions such as hypertension, depression or pain.

Also, as indicated above, the compounds disclosed hereunder are useful as agents capable of lowering ocular hypertension without substantial undesirable side effects, such as hypotension and sedation at therapeutically effective doses.

OBJECTS OF THE INVENTION

It is an object of the invention to provide compounds and compositions useful in treating disorders modulated by alpha-2 adrenoreceptors.

It is an object of this invention to provide novel compounds having substantial analgesic activity in the treatment of chronic pain, regardless of origin. Chronic pain may be, without limitation, visceral, inflammatory or neuropathic in origin. Such chronic pain may arise as a result of, or be attendant to, conditions including without limitation: arthritis, (including rheumatoid arthritis), spondylitis, gouty arthritis, osteoarthritis, juvenile arthritis, and autoimmune diseases including, without limitation, lupus erythematosus.

These compositions can also be used within the context of the treatment of chronic gastrointestinal inflammations, Crohn's disease, gastritis, irritable bowel disease (IBD) and ulcerative colitis; and in treatment of visceral pain, including pain caused by cancer or attendant to the treatment of cancer as, for example, by chemotherapy or radiation therapy.

These compositions can be used within the context of the treatment of other chronic pain symptoms, and especially in the treatment of chronic forms of neuropathic pain, in particular, without limitation, neuralgia, herpes, deafferentation pain, and diabetic neuropathies.

It is also an object of this invention to provide novel compounds for treating ocular disorders, such as ocular hypertension, glaucoma, hyperemia, conjunctivitis and uveitis. Preferably, such compounds are therapeutically effective for the treatment of ocular hypertension without causing agents capable of lowering ocular hypertension without substantial undesirable side effects, such as hypotension and sedation at therapeutically effective doses.

It is also an object of this invention to provide novel compounds for treating the pain associated with substance abuse and/or withdrawal.

It is a still further object of this invention to provide such compounds which have good activity when delivered by peroral, parenteral, intranasal, ophthalmic, and/or topical dosing, or injection.

It is also an object of this invention to provide methods of treating pain through the therapeutic administration of the compounds disclosed herein.

It is further an object of the present invention to provide methods of treating conditions known to be susceptible to treatment through alpha 2 adrenergic receptors without the deleterious side effects characteristic of such agents, such as hypotension and sedation at therapeutically effective doses.

SUMMARY OF THE INVENTION

The present invention is directed to compounds having the formula:

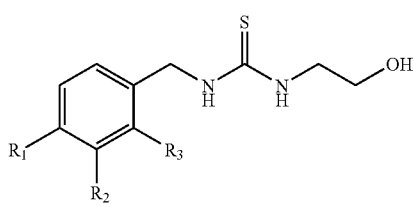

wherein $R_1$ is F or H, $R_2$ is Cl or H, and $R_3$ is F or H; and wherein if $R_1$ is F then $R_2$ and $R_3$ are both H; and if $R_1$ is H then $R_2$ is Cl and $R_3$ is F, and alkyl esters thereof, and pharmaceutically acceptable salts of these compounds.

The invention is also directed to methods of treating pain, particularly chronic pain, through the administration of pharmaceutically effective amounts of compounds of the above structure.

The present invention is also directed to methods of treating pathological ocular conditions, such as ocular hypertension, through the treatment of a patient suffering from such condition with the compounds disclosed hereunder.

Further, the invention is directed to methods of treating glaucoma through the administration of a pharmaceutically effective amount of these compounds.

DETAILED DESCRIPTION OF THE INVENTION

In one aspect, the present invention is directed to compounds of Formula 1:

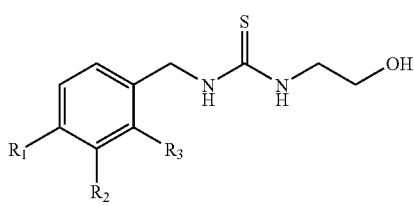

wherein $R_1$ is F or H, $R_2$ is Cl or H, and $R_3$ is F or H; and wherein if $R_1$ is F then $R_2$ and $R_3$ are both H; and if $R_1$ is H then $R_2$ is Cl and $R_3$ is F, and alkyl esters thereof, and pharmaceutically acceptable salts of these compounds.

Preferred compounds corresponding to this structure are the following compound (hereinafter termed Formula 2):

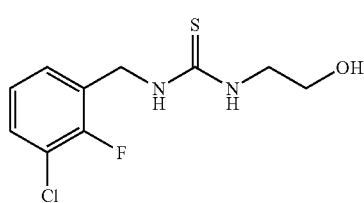

Formula 2 and the following compound (hereinafter termed Formula 3):

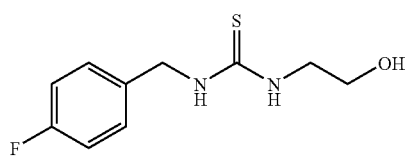

Formula 3 and their alkyl esters, and pharmaceutically acceptable derivatives and/or salts of these compounds.

Applicants have discovered that these compounds activate $\alpha_2$ receptors, particularly $\alpha_{2B}$ receptors. Additionally, these compounds act as a highly effective analgesic, particularly in chronic pain models, with minimal undesirable side effects, such as sedation and cardiovascular depression, commonly seen with agonists of the $\alpha_2$ receptors.

Such compounds may be administered at pharmaceutically effective dosages. Such dosages are normally the minimum dose necessary to achieve the desired therapeutic effect; in the treatment of chronic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

When used for the treatment of an ocular pathology such as ocular hypertension, it may be desirable to formulate the drug as a topical agent to be instilled into the eye. Such formulations may contain the active ingredient in a concentration range of approximately 0.0001 to 0.1 percent weight by volume. The composition itself includes, in addition to the active ingredient, such excipients which are per se well know in the art for preparing ophthalmic compositions, particularly ophthalmic solutions. In accordance with the method of the invention the ophthalmic compositions, preferably ophthalmic solutions are applied topically to the mammalian eye approximately 1 or 2 times daily.

For reducing intraocular pressure in a mammalian eye, and particularly for treatment of glaucoma in humans suffering from that condition, the active compounds (or mixtures or salts thereof) are administered in accordance with the present invention to the eye admixed with an ophthalmically acceptable carrier. Any suitable, e.g., conventional, ophthalmically acceptable carrier may be employed. A carrier is ophthalmically acceptable if it has substantially no long term or permanent detrimental effect on the eye to which it is administered. Examples of ophthalmically acceptable carriers include water (distilled or deionized water) saline solutions, and other aqueous media. In accordance with the invention, the active compounds are preferably soluble in the carrier which is employed for their administration, so that the active compounds are administered to the eye in the form of a solution. Alternatively, a suspension of the active compound or compounds (or salts thereof) in a suitable carrier may also be employed.

In accordance with the invention the active compounds (or mixtures or salts thereof) are administered in an ophthalmically acceptable carrier in sufficient concentration so as to deliver an effective amount of the active compound or compounds to the eye. Preferably, the ophthalmic, therapeutic solutions contain one or more of the active compounds in a concentration range of approximately 0.0001% to approximately 0.1% (weight by volume) and more preferably approximately 0.0005% to approximately 0.1% (weight by volume).

In this embodiment of the invention, any method of administering drugs directly to a mammalian eye may be employed to administer, in accordance with the present invention, the active compound or compounds to the eye to be treated. By the term "administering directly" is meant to exclude those general systemic drug administration modes, e.g., injection directly into the patient's blood vessels, oral administration and the like, which result in the compound or compounds being systemically available. The primary effect on the mammal resulting from the direct administering of the active compound or compounds to the mammal's eye is preferably a reduction in intraocular pressure. More preferably, the active useful compound or compounds are applied topically to the eye or are injected directly into the eye. Particularly useful results are obtained when the compound or compounds are applied topically to the eye in an ophthalmic solution (ocular drops). Topical ophthalmic preparations, for example ocular drops, gels or creams, are preferred because of ease of application, ease of dose delivery, and fewer systemic side effects, such as cardiovascular hypotention. An exemplary topical ophthalmic formulation may be as follows (the abbreviation q.s. means a quantity sufficient to effect the result or to make volume): about 0.0001% to about 0.1% of the active compound in accordance with the present invention; about 0-0.1% (w/v) of a ophthalmologically acceptable preservative; about 0-40% (w/v) of a suitable vehicle; about 1-10% (w/v) of a tonicity adjuster; about 0.01%-10% (w/v) of a physiologically acceptable buffer; about antioxidant, if necessary to preserve the stability of the active agent; and water to 100% (w/v).

Various preservatives may be used in the ophthalmic preparation described above. Preferred preservatives include, but are not limited to, benzalkonium chloride, chlorobutanol, thimerosal, phenylmercuric acetate, stabilized and unstabilized chlorine dioxide, such as Purite®, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjusters may be added as needed or convenient. They include, but are not limited to, salts, particularly sodium chloride, potassium chloride, mannitol, and glycerin, or any other suitable ophthalmically acceptable tonicity adjuster.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

The ophthalmic solution (ocular drops) may be administered to the mammalian eye as often as necessary to maintain an acceptable level of intraocular pressure in the eye. In other words, the ophthalmic solution (or other formulation) which contains the therapeutic agent as the active ingredient, is administered to the mammalian eye as often as necessary to maintain the beneficial hypotensive effect of the active ingredient in the eye. Those skilled in the art will recognize that the frequency of administration depends on the precise nature of the active ingredient and its concentration in the ophthalmic formulation. Within these guidelines it is contemplated that the ophthalmic formulation of the present invention will be administered to the mammalian eye approximately once or twice daily.

Additionally, the therapeutic agents of this patent application may be formulated for use with biocompatible implants, such as intraocular and subconjunctival implants, for the treatment of ocular hypertension. Such implants are well known in the art and 4 examples of such implants may be found described in, e.g., U.S. Pat. Nos. 5,443,505; 5,766,242; 5,824,072; and 5,869,079, which are incorporated by reference herein.

Another aspect of the invention is drawn generally to therapeutic compositions comprising the compounds of Formula 1 and alkyl esters and pharmaceutically acceptable derivatives and/or salts of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as a excipient or vehicle for the active compound. The formulations may also include wetting agents, emulsifying agents, preserving agents, sweetening agents, and/or flavoring agents. If used as in an ophthalmic or infusion format, the formulation will usually contain one or more salt to influence the osmotic pressure of the formulation.

In another aspect, the invention is directed to methods for the treatment of pain, particularly chronic pain, through the administration of a compound of Formula 1, and pharmaceutically acceptable alkyl esters, salts, and derivatives thereof to a mammal in need thereof. As indicated above, the compound will usually be formulated in a form consistent with the desired mode of delivery.

It is known that chronic pain (such as pain from cancer, arthritis, and many neuropathic injuries) and acute pain (such as that pain produced by an immediate mechanical stimulus, such as tissue section, pinch, prick, or crush) are distinct neurological phenomena mediated to a large degree either by different nerve fibers and neuroreceptors or by a rearrangement or alteration of the function of these nerves upon chronic stimulation. Sensation of acute pain is transmitted quite quickly, primarily by afferent nerve fibers termed C fibers, which normally have a high threshold for mechanical, thermal, and chemical stimulation. While the mechanisms of chronic pain are not completely understood, acute tissue injury can give rise within minutes or hours after the initial stimulation to secondary symptoms, including a regional reduction in the magnitude of the stimulus necessary to elicit a pain response. This phenomenon, which typically occurs in a region emanating from (but larger than) the site of the original stimulus, is termed hyperalgesia. The secondary response can give rise to profoundly enhanced sensitivity to mechanical or thermal stimulus.

The A afferent fibers (Aβ and Aδ fibers) can be stimulated at a lower threshold than C fibers, and appear to be involved in the sensation of chronic pain. For example, under normal conditions, low threshold stimulation of these fibers (such as a light brush or tickling) is not painful. However, under certain conditions such as those following nerve injury or in the herpesvirus-mediated condition known as shingles the application of even such a light touch or the brush of clothing can be very painful. This condition is termed allodynia and appears to be mediated at least in part by Aβ afferent nerves. C fibers may also be involved in the sensation of chronic pain, but if so it appears clear that persistent firing of the neurons over time brings about some sort of change which now results in the sensation of chronic pain.

By "acute pain" is meant immediate, usually high threshold, pain brought about by injury such as a cut, crush, burn, or by chemical stimulation such as that experienced upon exposure to capsaicin, the active ingredient in chili peppers.

By "chronic pain" is meant pain other than acute pain, such as, without limitation, neuropathic pain, visceral pain (including that brought about by Cron's disease and irritable bowel syndrome (IBS)), and referred pain.

EXAMPLES

Example 1

Synthesis of 1-(3-chloro-2-fluorobenzyl)-3-(2-hydroxyethyl)-thiourea (Formula 2)

One molar equivalent of 3-chloro-2-fluoro-benzyl bromide (commercially available from e.g., Lancaster Synthesis, Ltd.) is permitted to react with 2 molar equivalents of potassium isothiocyanate in dimethylformamide (DMF) containing 0.5 molar equivalent of NaI at 90° C. for 5 hours with stirring to yield 3-chloro-2-fluorobenzyl isothiocyanate. The reaction mixture is permitted to cool to room temperature, and the solution is diluted with H20 and extracted with ether. The ether phase containing the product is removed and the reaction mixture extracted twice more with fresh ether. The ether phases are combined and the product is concentrated in a Speed Vac® vacuum centrifuge (using house vacuum) set in a water bath at about 45° C. When the ether has evaporated, the unpurified 3-chloro-2-fluorobenzyl isothiocyanate is a viscous liquid.

3.57 g of this compound is mixed with 3 molar equivalents of ethanolamine in acetonitrile, and a catalytic amount (less than 1%) of DMAP (N—N-dimethyl amino pyridine) is added. The reaction mixture is incubated for 14 hours at room temperature with constant stirring. The resulting solution is then concentrated using the Speed Vac® vacuum centrifuge in a 60° C.-70° C. water bath.

The product, 1-(3-chloro-2-fluorobenzyl)-3-(2-hydroxyethyl)-thiourea, is purified by liquid chromatography using 200-300 mesh silica gel in a glass column. The concentrated reaction solution is applied to the column and the column washed with three column volumes of Solvent A (50% ethyl acetate/50% hexanes). The product is then eluted using 2-3 column volumes of Solvent B (10% methanol/90% ethyl acetate). The eluted product is again concentrated in a Speed Vac® vacuum centrifuge to remove the solvent. The product is then permitted to stand at room temperature, where is crystallizes spontaneously. The crystals are stored in the freezer at −78° C.

The product has the following spectroscopic characteristics: $^1$H NMR (D$_6$ DMSO, 300 MHz) δ 7.98 (br s, 1H), 7.63 (br s, 1H), 7.46 (t, J=3.9 Hz, 1H), 7.32-7.18 (m, 2H), 4.78 (br s, 1H), 4.72 (d, J=3.9 Hz, 2H), 3.47 (br s, 4H).

In order to compare the biological activity of 1-(3-chloro-2-fluorobenzyl)-3-(2-hydroxyethyl)-thiourea with that of the 2-fluorobenzyl derivative (FORMULA 4) and the 4-flurobenzyl derivative (FORMULA 3), FORMULA 4 is synthesized using 2-fluoro-benzyl bromide (also commercially available) as the starting material. FORMULA 3 is synthesized using commercially purchased 4-fluorobenzyl isothiocyanate. Other synthetic steps are analogous to those used above to synthesize the compound of FORMULA 2.

The 2-fluorobenzyl isothiourea derivative (hereinafter termed FORMULA 4) has the following formula:

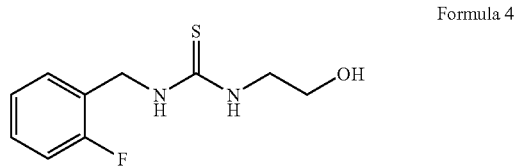

Formula 4

The physiological activity of these compounds was tested using four models: a rat locomotor model to assess sedation, an assay of cardiovascular activity in monkeys, a rat thermal paw withdrawal assay (Dirig et al., *J. Neurosci. Methods* 76:183-191 (1997) to test the alleviation of acute pain, and the rat spinal nerve ligation allodynia model (Kim and Chung, *Pain* 50:355-363 (1992) to assess the alleviation of neuropathic pain and central sensitization typical of chronic pain. As is known to those of skill in the art, these tests are established pharmacological methods for determining sedation, cardiovascular effects, acute pain and chronic pain, respectively, of pharmaceutical agents.

Example 2

Sedative Activity

To test sedation, six male Sprague-Dawley rats were given up to 3 mg/kg of each compound in a saline or DMSO vehicle by intraperitoneal injection (i.p.). Sedation was graded 30 minutes following administration of the drug by monitoring locomotor skills as follows.

The Sprague-Dawley rats are weighed and 1 ml/kg body weight of an appropriate concentration (ie. 3 mg/ml for a final dose of 3 mg/kg) drug solution is injected intraperitoneally. FORMULA 3 is formulated in approximately 10% DMSO and FORMULA 2 and FORMULA 4 are formulated in 50% DMSO. The results are compared to 29 historical controls that were injected with 1 ml/kg saline or 50% DMSO. Rat activity is then determined 30 minutes after injection of the drug solution. Rats are placed in a dark covered chamber and a digicom analyzer (Omnitech Electronic) quantitates their exploratory behavior for a five-minute period. The machine records each time the rat interrupts an array of 32 photoelectric beams in the X and Y orientation.

The results show that, in comparison to the appropriate vehicle controls, none of the compounds caused a statistically significant reduction in the exploratory activity of the rats. FORMULA 2 and FORMULA 3 were tested at 1 mg/kg and FORMULA 4 was tested at 3 mg/kg. Thus, the compounds are not sedating.

Example 3

Effects on Cardiovascular System

To test the effect of the compounds on the cardiovascular system, six cynomolgus monkeys were given 500 µg/kg of each compound by intravenous injection (i.v.). The effects of each compound on the animals' blood pressure and heart rate was measured at time intervals from 30 minutes to six hours following administration of the drug. The peak change from a baseline measurement taken 30 minutes before drug administration is recorded using a blood pressure cuff modified for use on monkeys.

The monkeys are weighed (approximately 4 kg) and an appropriate volume (0.1 ml/kg) of a 5 mg/ml solution of each compound formulated in 10% DMSO is injected into the cephalic vein in the animals' arms. Cardiovascular measurements are made with a BP 100S automated sphygmomanometer (Nippon Colin, Japan) at 0.5, 1, 2, 4 and 6 hours.

The results show that, in comparison to the predrug control, none of the compounds have any detectable effect on the cardiovascular system.

Example 4

Alleviation of Acute Pain

Models to measure sensitivity to acute pain have typically involved the acute application of thermal stimuli; such a stimulus causes a programmed escape mechanism to remove the affected area from the stimulus. The proper stimulus is thought to involve the activation of high threshold thermoreceptors and C fiber dorsal root ganglion neurons that transmit the pain signal to the spinal cord.

The escape response may be "wired" to occur solely through spinal neurons, which receive the afferent input from the stimulated nerve receptors and cause the "escape" neuromuscular response, or may be processed supraspinally—that is, at the level of the brain. A commonly used method to measure nociceptive reflexes involves quantification of the withdrawal or licking of the rodent paw following thermal excitation. See Dirig, D. M. et al., *J. Neurosci. Methods* 76:183-191 (1997) and Hargreaves, K. et al., *Pain* 32:77-88 (1988), hereby incorporated by reference herein.

In a variation of this latter model, male Sprague-Dawley rats were tested by being placed on a commercially available thermal stimulus device constructed as described in Hargreaves et al. This device consists of a box containing a glass plate. The nociceptive stimulus is provided by a focused projection bulb that is movable, permitting the stimulus to be applied to the heel of one or both hindpaws of the test animal. A timer is actuated with the light source, and the response latency (defined as the time period between application of the stimulus and an abrupt withdrawal of the hindpaw) is registered by use of a photodiode motion sensor array that turns off the timer and light. Stimulus strength can be controlled by current regulation to the light source. Heating is automatically terminated after 20 seconds to prevent tissue damage.

Four test animals per group were weighed (approximately 0.3 kg) and injected intraperitonealy (i.p.) with 1 ml/kg of each compound formulated in approximately 50% dimethylsulfoxide (DMSO) vehicle. Animals received a 0.3 mg/kg and a 3 mg/kg dose of the three compounds. Rats were acclimated to the test chamber for about 15 minutes prior to testing. The paw withdrawal latency was measured at 30, 60 and 120 minutes after drug administration. The right and left paws were tested 1 minute apart, and the response latencies for each paw were averaged. Stimulus intensity was sufficient to provide a temperature of 45-50 degrees centigrade to each rat hindpaw.

The results show that none of the compounds provide analgesic effects in this bioassay of acute pain. The response latencies for rats treated with the compounds were not statistically different from the response latencies of the rats treated with vehicle alone.

Example 5

Alleviation of Chronic Pain

A model for chronic pain (in particular peripheral neuropathy such as causalgia) involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to pain from low-threshold mechanical stimuli, such as that producing a faint sensation of touch in a human, within about 1 week following surgery. This sensitivity to normally non-painful touch is called "tactile allodynia" and lasts for at least two months. The response includes lifting the affected hindpaw to escape from the stimulus, licking the paw and holding it in the air for many seconds. None of these responses is normally seen in the control group.

Rats are anesthetized before surgery. The surgical site is shaved and prepared either with betadine or Novacaine. Incision is made from the thoracic vertebra X111 down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

A complete hemostasis is confirmed, then the wounds are sutured. A small amount of antibiotic ointment is applied to the incised area, and the rat is transferred to the recovery plastic cage under a regulated heat-temperature lamp. On the day of the experiment, at least seven days after the surgery, six rats per test group are administered the test drugs by intraperitoneal (i.p.) injection or oral gavage. For i.p. injection, the compounds are formulated in approximately 50% DMSO and given in a volume of 1 ml/kg body weight. FORMULA 2 was tested at doses ranging between 1 and 300 µg/kg, FORMULA 3 was tested at doses between 0.1 and 3 mg/kg and FORMULA 4 was tested at doses of 0.3 and 3 mg/kg. FORMULA 2 was also administered by oral gavage at doses of 0.1, 0.3 and 1 mg/kg body weight to 24-hour fasted rats. A volume equal to 1 ml/kg body weight of an appropriate concentration (ie. 1 mg/ml for a 1 mg/kg dose) of FORMULA 2 formulated in approximately 50% DMSO was injected using an 18-gauge, 3-inch gavage needle that is slowly inserted through the esophagus into the stomach.

Tactile allodynia is measured prior to and 30 minutes after drug administration using von Frey hairs that are a series of fine hairs with incremental differences in stiffness. Rats are placed in a plastic cage with a wire mesh bottom and allowed to acclimate for approximately 30 minutes. The von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., *Ann. Rev. Pharmacol. Toxicol.* 20:441-462 (1980). The post-drug threshold is compared to the pre-drug threshold and the percent reversal of tactile sensitivity is calculated based on a normal threshold of 15.1 grams.

The results showed that FORMULA 4 had no analgesic activity at doses up to 3 mg/kg. Surprisingly, AGN196204 and FORMULA 2 were both able to reduce the response to the tactile stimuli that indicate tactile allodynia. FORMULA 3 reversed the allodynic pain by 34% at an i.p. dose of 0.3 mg/kg, 32% at 1 mg/kg and 26% at 3 mg/kg. FORMULA 2 reversed the allodynia by 55% at an i.p. dose of 3 μg/kg, 85% at 10 μg/kg, 90% at 30 μg/kg, 95% at 100 μg/kg and 92% at 300 μg/kg. The oral doses of FORMULA 2 ranging from 0.1 to 1 mg/kg alleviated the allodynic pain by 82-86%. Thus, FORMULA 3 and FORMULA 2 are analgesic in a model of chronic pain.

Example 6

Treatment of Allodynia with FORMULA 3

A 50 year old male in generally good physical condition suffers from serious pain to his upper body due caused by contact of his skin with his clothing. The patient is unable to wear clothing on his upper body without severe pain. His symptoms suggest a diagnosis of shingles.

The patient is given a therapeutically effective oral dose of FORMULA 3 in capsule form as needed for the treatment of pain. Following two day's treatment, the patient reports that the allodynia resulting from shingles is markedly reduced, and that he is able to wear clothing on his upper body with greater comfort.

Example 6

Treatment of Allodynia with FORMULA 2

Same facts as in Example 5, except the patient is given a therapeutically effective oral dose of FORMULA 2 in capsule form as needed for the treatment of pain. Following two day's treatment, the patient reports that the allodynia resulting from shingles is markedly reduced, and that he is able to wear clothing on his upper body with greater comfort.

Example 7

Treatment of Visceral Pain with FORMULA 3

A 43 year old female patient suffering from colon cancer and undergoing chemotherapy experiences severe visceral pain associated with this primary condition. Treatment of this pain with opiates has been ineffective to provide substantial relief.

The patient is given a therapeutic amount of FORMULA 3 by intravenous infusion in a pharmaceutically acceptable vehicle. The treatment is given twice daily. After two days the patient reports a significant alleviation in the visceral pain associated with her condition.

Example 8

Treatment of Visceral Pain with FORMULA 2

Under the same facts as Example 7, except the patient is given FORMULA 2 instead of FORMULA 3. After two days the patient reports a significant alleviation in the visceral pain associated with her condition.

Example 9

Treatment of Ocular Hypertension with FORMULA 2

African Green monkeys are made glaucomatous and divided into three groups. Ocular hypertension is measured before the administration of any drug, then one of each group of animals is given an oral dose of either a) glucose (negative control); b) a formulation of FORMULA 2 at a dosage of either 2 mg/kg or 7 mg/kg, or c) Diamox® (acetazolamide; a carbonic anhydrase inhibitor used for treatment of glaucoma) (positive control) at a concentration of 20 mg/kg. Intraocular pressure is measured at 0, 6, 12, and 24 hours following administration of each formulation.

The results are as indicated in the following table:

| | Change in Intraocular Pressure (%) | | | |
|---|---|---|---|---|
| | Glucose | FORMULA 2 (7 mg/kg) | FORMULA 2 (2 mg/kg) | Diamox ® |
| 0 hours | 0% | 0% | 0% | 0% |
| 6 hours | −2% | −22% | −18% | −38% |
| 12 hours | −12% | −26% | −32% | −41% |
| 24 hours | +2% | −15% | −3% | −18% |

The examples contained herein are intended to be exemplary only, and do not limit the scope of the invention, which is defined by the claims that conclude this specification.

We claim:

1. A method of treating glaucoma in a mammal in need thereof comprising the step: administering to said patient a therapeutically effective dose of a composition comprising a compound represented by the formula:

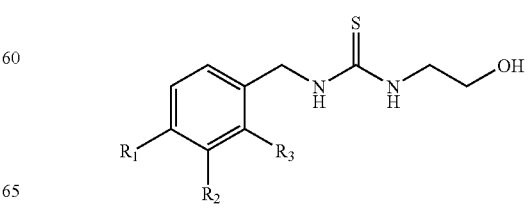

wherein R1 is F or H, R2 is Cl or H, and R3 is F or H; and wherein if R1 is F then R2 and R3 are both H; and if R1 is H then R2 is Cl and R3 is F, and pharmaceutically acceptable salts of these compounds.

2. The method of claim 1 wherein said compound is represented by the formula:

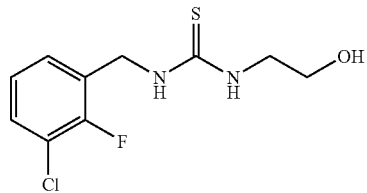

and pharmaceutically acceptable salts of these compounds.

3. The method of claim 1 wherein said compound is represented by the formula

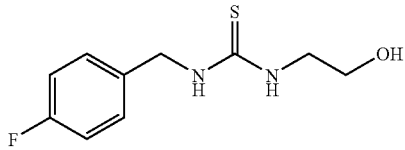

and pharmaceutically acceptable salts of these compounds.

* * * * *

UNITED STATES PATENT AND TRADEMARK OFFICE
CERTIFICATE OF CORRECTION

| | | |
|---|---|---|
| PATENT NO. | : 7,754,768 B2 | Page 1 of 1 |
| APPLICATION NO. | : 12/024609 | |
| DATED | : July 13, 2010 | |
| INVENTOR(S) | : Ken Chow et al. | |

It is certified that error appears in the above-identified patent and that said Letters Patent is hereby corrected as shown below:

In column 7, line 34, delete "Cron's" and insert -- Crohn's --, therefor.

In column 10, line 43, delete "Novacaine." and insert -- Novocaine. --, therefor.

Signed and Sealed this

Twelfth Day of October, 2010

David J. Kappos
*Director of the United States Patent and Trademark Office*